United States Patent
Franzmann et al.

(10) Patent No.: US 6,736,923 B1
(45) Date of Patent: May 18, 2004

(54) PROCESS FOR MANUFACTURING DISPOSABLE ABSORBENT CORES, AND AN APPARATUS FOR PERFORMING THE PROCESS

(75) Inventors: Dirk Franzmann, Cincinnati, OH (US); Christoph Johann Schmitz, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 186 days.

(21) Appl. No.: 09/979,495

(22) PCT Filed: Jun. 23, 2000

(86) PCT No.: PCT/US00/17500
§ 371 (c)(1),
(2), (4) Date: Jan. 31, 2002

(87) PCT Pub. No.: WO01/00123
PCT Pub. Date: Jan. 4, 2001

(30) Foreign Application Priority Data

Jun. 25, 1999  (EP) .............................................. 99112229

(51) Int. Cl.$^7$ .............................................. B32B 31/00
(52) U.S. Cl. ........................ 156/265; 156/270; 156/301; 156/302; 156/512; 156/519; 156/552; 156/559
(58) Field of Search ................................. 156/264, 265, 156/270, 303, 302, 300, 301, 299, 512, 518, 519, 520, 552, 560, 559

(56) References Cited

U.S. PATENT DOCUMENTS

| | | | |
|---|---|---|---|
| 4,673,402 A | 6/1987 | Weisman et al. | |
| 4,760,764 A | 8/1988 | De Jonckheere et al. | |
| 4,935,022 A | 6/1990 | Lash et al. | |
| 5,147,345 A | 9/1992 | Young et al. | |
| 5,584,954 A | 12/1996 | van der Klugt | |
| 5,660,665 A | 8/1997 | Jalonen | |
| 5,683,533 A | * 11/1997 | Keighley et al. | 156/204 |
| 5,705,013 A | * 1/1998 | Nease et al. | 156/260 |
| 5,824,178 A | * 10/1998 | Shingu et al. | 156/265 |

FOREIGN PATENT DOCUMENTS

| | | |
|---|---|---|
| EP | 0 652 175 A1 | 5/1995 |
| WO | WO 96/21411 | 7/1996 |

* cited by examiner

*Primary Examiner*—Linda Gray
(74) *Attorney, Agent, or Firm*—Michael S. Kolodesh; Jay A. Krebs; Ken K. Patel

(57) ABSTRACT

This invention provides a process and apparatus (38) for the manufacture of disposable absorbent cores from a continuous web (40), wherein a plurality of first and second core elements (40a, 40b) are cut from the same continuous web (40). The object of the invention is achieved by rotating each of first and second core elements (40a, 40b) about axes perpendicular to the plane of the core element and subsequently combining a first core element (40a) and a second core element (40b) in proximal relationship to form the absorbent core. Preferably each of the first and second core elements (40a, 40b) are rotated through 90° in mutually counter-rotating directions.

8 Claims, 5 Drawing Sheets

PROCESS FOR MANUFACTURING DISPOSABLE ABSORBENT CORES, AND AN APPARATUS FOR PERFORMING THE PROCESS

The invention relates to a process for manufacturing profiled disposable absorbent cores, without waste of the absorbent core material; and to an apparatus for performing the process. In particular, diapers or training pants may be made by the process of the invention having absorbent cores with an hourglass-shape for better fit around the legs of the wearer, but the process may also be applied to feminine hygiene articles, adult incontinence articles, and other disposable absorbent articles.

Disposable absorbent articles have become very popular in the market place today. Many of these articles include features such as absorbent cores providing a variety of functions including improved containment characteristics and better, more comfortable fit.

An overriding consideration in the construction of a disposable absorbent article is the cost of manufacturing the article, including the materials cost. The present invention provides methods for manufacturing absorbent cores for absorbent articles with little or no wasted material. Thus, the absorbent cores made by the process of the present invention can be provided at relatively lower cost than many of the absorbent cores that are currently manufactured using techniques in which material is wasted. Processes which reduce or avoid material waste are disclosed in the following references.

U.S. Pat. No. 4,760 764, issued on $2^{nd}$ Aug. 1988, relates to manufacturing methods for disposable diapers which have an "egg-timer" profile. It is proposed to reduce production costs by making effective use of the absorbent core, and in particular by avoiding waste by cutting out and throwing away a part of the absorbent core. This is achieved by providing "nested panels" in a single side panel web and then rearranging the panels, for example as shown in FIG. 4 of the patent to form an absorbent pad.

WO96/21411, published on $18^{th}$ Jul. 1996, discloses a method for manufacturing shaped or contoured absorbent cores made from multiple pieces or layers. Wherein the multiple pieces or layers are cut from the same continuous web with "zero scrap".

It is an object of the present invention to provide an alternative method of achieving waste-saving benefits, and associated reduction of material costs.

The invention provides a process and apparatus for the manufacture of disposable absorbent cores from a continuous web, wherein a plurality of first and second core elements, are cut from the same continuous web.

SUMMARY OF THE INVENTION

The object of the invention is achieved by rotating each of first and second core elements about axes perpendicular to the plane of the core element and subsequently combining a first core element and a second core element in proximal relationship to form the absorbent core. Preferably each of the first and second core elements are rotated through 90° in mutually counter-rotating directions.

BRIEF DESCRIPTION OF THE DRAWINGS

FIG. 5b shows a plan view of an absorbent core made by combining a first core element and a second core element of FIG. 5a.

DETAILED DESCRIPTION OF THE INVENTION

Figure 1:
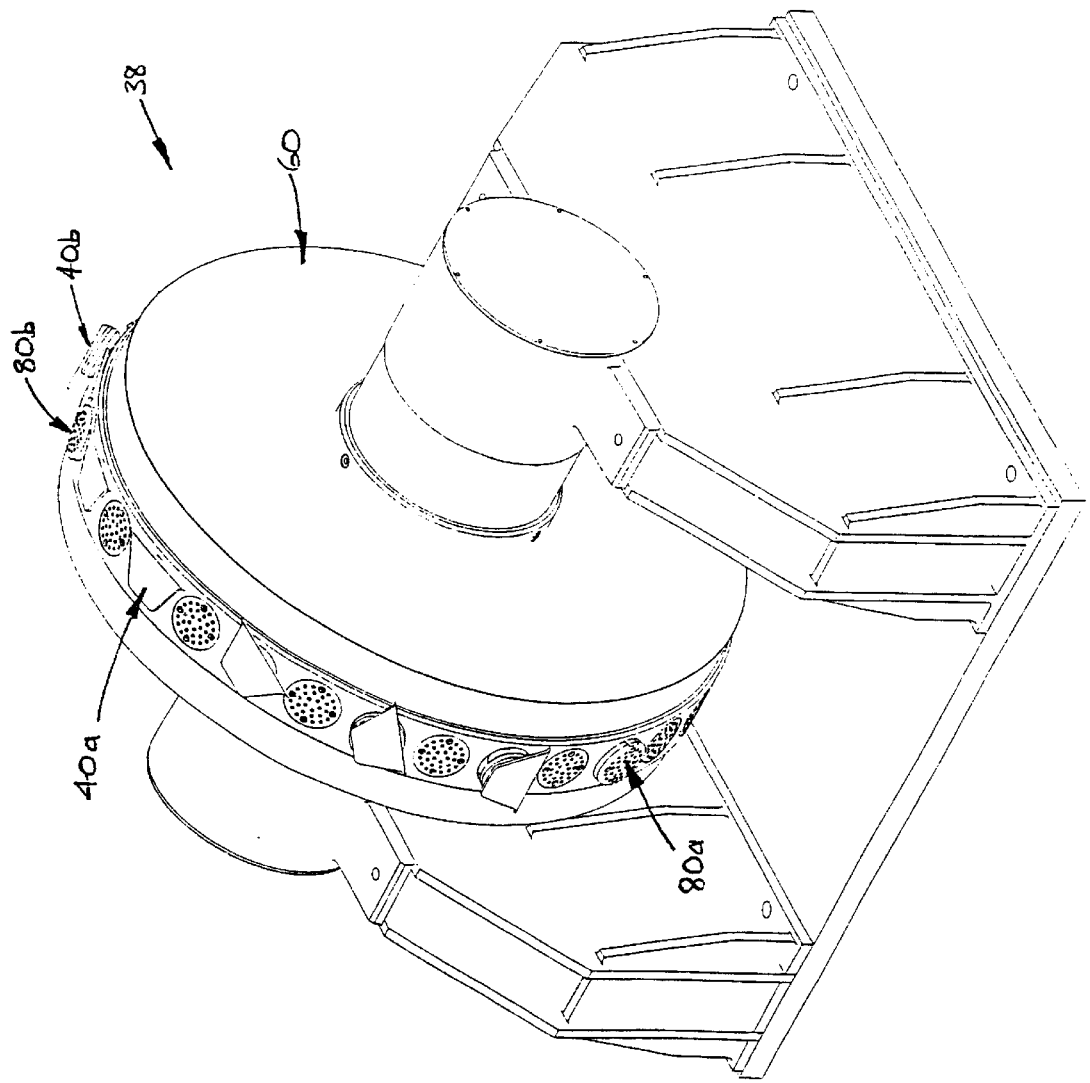
FIG. 1 shows a perspective view of an apparatus for use in the process of the present invention.

Incontinence management articles, such as non-cloth disposable diapers, have traditionally utilized absorbent structures which comprise entangled masses of fibers, i.e. non woven fibrous webs. These webs imbibe aqueous fluids, including discharged body fluids, both by an absorption mechanism where fluid is taken up by the fiber material itself, and especially by a wicking mechanism where fluid is acquired by, distributed through and stored in the capillary interstices between the fibers. These webs often comprise loosely compacted, low density layers of absorbent fibers, such as carded cotton webs, air-laid cellulose fibers, comminuted wood pulp fibers, and the like. Fibrous webs used in such absorbent articles also often include certain absorbent gelling materials usually referred to as "hydrogels", "super absorbent" or "hydrocolloid" materials to store large quantities of the discharged body fluids. Known technology to manufacture such cores includes air laying the fibers into shaped cavities on a screened drum to form the shape of the core and control the quantity of material used per core. Excess overfill of the shaped cavities is removed and returned to the incoming air stream by a scarfing roll. The Absorbent Gelling Materials (AGM) are added to the airstream along with the fiber materials. This process allows for many alternative shapes to be produced via changes in screen, laydown drum, configuration. Therefore the shape of the material is achieved via "molding" the fibers into shaped cavities. This process provides shape without trim, which in turn results in minimal scrap. Examples of such cores are disclosed in U.S. Pat. No. 4,673,402, issued $16^{th}$ Jun. 1987 and U.S. Pat. No. 4,935,022, issued $19^{th}$ Jun. 1990.

An alternative absorbent material potentially capable of providing capillary fluid transport would be open-celled polymeric foams. If made appropriately, open-celled polymeric foams could provide features of capillary fluid acquisition, transport and storage required for use in high performance absorbent cores for absorbent articles such as diapers. Absorbent articles containing such foams could possess desirable wet integrity, could provide suitable fit throughout the entire period the article is worn, and could avoid changes in shape during use. In addition, absorbent articles containing such foam structures could be easier to manufacture on a commercial scale. For example, absorbent diaper cores could simply be stamped out of continuous foam sheets and could be designed to have considerably greater integrity and uniformity than air-laid fibrous absorbent cores containing particulate absorbent gelling materials.

Shaped or contoured absorbent cores made from open-celled foam materials are disclosed in U.S. Pat. No. 5,147, 345, issued $15^{th}$ Sep. 1992. This patent discloses absorbent cores comprising a fluid acquisition/distribution component that can be fibrous or foam based, as well as fluid storage/redistribution component that comprises a hydrophilic, flexible, open-celled polymeric foam. FIG. 9 discloses one such shaped or contoured core having an hourglass-shaped fluid redistribution/storage layer comprising an open-cell absorbent foam. Forming shaped or contoured absorbent cores or layers from foam materials is not without problems. The hourglass-shaped foam layer is typically made from a single rectangular piece of foam. This rectangular piece of foam can be notched, cut or otherwise severed from the hourglass-shaped piece. In carrying out these operations, a significant amount of unusable foam scrap can be created. Indeed it has been found that, in forming hourglass-shaped foam pieces, as much as 15% to 25% of the total foam material used can end up as unusable scrap.

The present invention relates to a process and apparatus for manufacturing an absorbent core having "zero scrap", thus eliminating the steps for disposing or recycling surplus material.

FIG. 1 shows a perspective view of an apparatus 38 according to the present invention. The apparatus comprises a rotating drum 60. The drum 60 applies discrete first and second core elements 40a, 40b to a receiving web 1. In FIG. 1 an incoming web 40 is fed to the apparatus 38 and is cut in a nested pattern (see, for example, FIG. 5), and the discrete first and second core elements 40a, 40b of the incoming webs are held on vacuum shells 80a, 80b which are arranged around the circumference of the rotating drum 60. The receiving web 1; the incoming web 40; and the cutting roll 39 are not shown in FIG. 1 to simplify this illustration.

The drum 60 is rotated about a main axis of the apparatus. In the embodiment illustrated in FIGS. 1, 2, 3a and 3b the main axis is oriented horizontally, but this main axis need not necessarily be horizontal in all cases.

The vacuum shells 80a, 80b are mounted on rotatable shafts 81 and are rotatable about an axis A which is radial with respect to the drum 60. Alternate vacuum shells 80a, 80b are rotatable in mutually counter-rotating directions, preferably plus and minus 90° from the starting position. The means for providing the rotation each of the rotatable shafts 81 may suitably be provided by a rack and pinion arrangement, and a cam follower which runs around a shell turning cam. The shell turning cam is shaped so that the rack and pinion operate to rotate alternate vacuum shells 80b through 90° during a first part of the cycle, prior to transfer of the second core element, 40b of the incoming web to the receiving web 1, and then return the vacuum shells 80b to their original orientation by rotating them back through minus 90° during a second part of the cycle after the transfer.

In addition, during the first part of the cycle, a shell lifting cam acts to "lift" the vacuum shell 80b radially outwards from the drum 60. This action helps to apply the second core element 40b of the incoming web 40 to the receiving web 1 at a transfer step. During the second part of the cycle, after the cut core element 40b of the incoming web has been transferred to the receiving web 1, the vacuum shells 80b are "withdrawn" radially inwards with respect to the drum 60. During the second part of the cycle, or subsequent to the second part of the cycle, the vacuum shells 80a (i.e. those vacuum shells which have not been rotated during the first part of the cycle) are rotated through minus 90° and are "lifted" radially outwards from the drum 60. This action helps to apply the first core elements 40a of the incoming web 40 to the receiving web 1 at a transfer step. Finally the vacuum shells 80a are "withdrawn" radially inwards with respect to the drum 60, and the cycle is ready to repeat.

Figure 2:
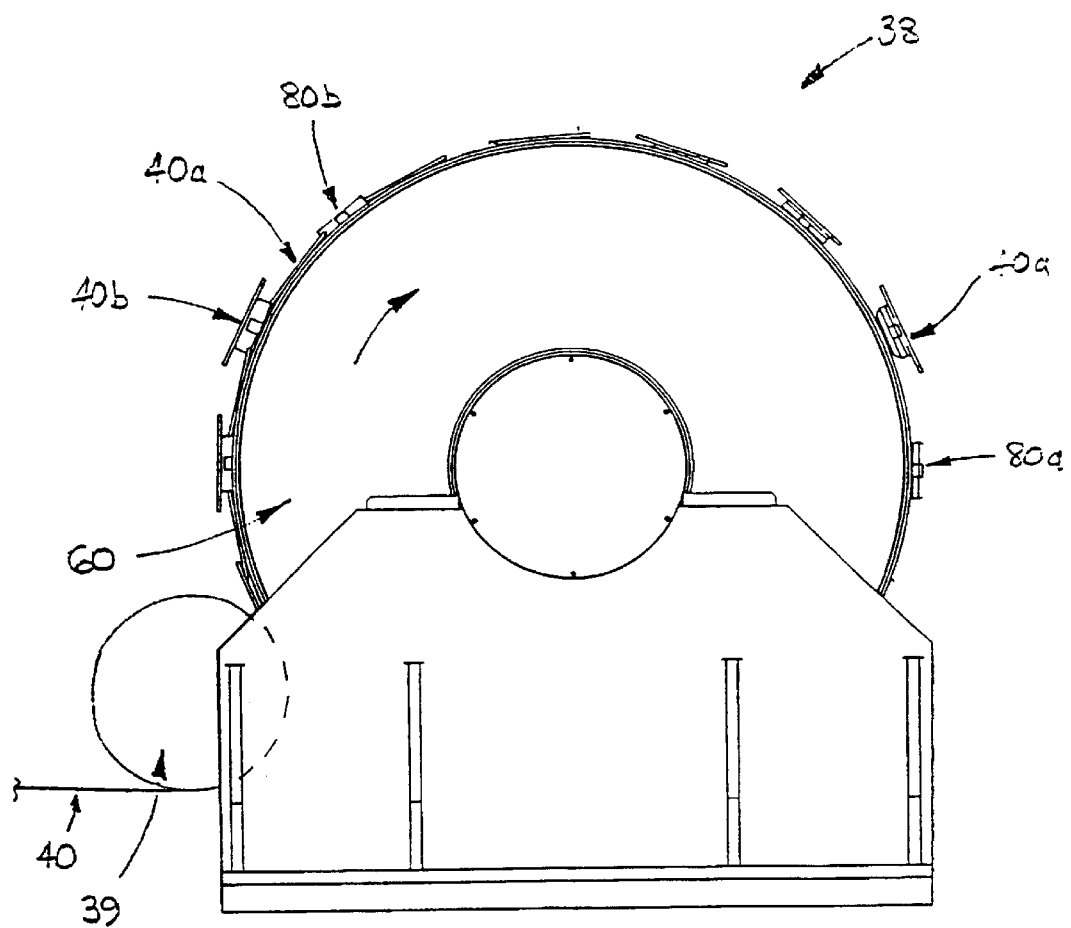
FIG. 2 shows a side elevation view of the apparatus of FIG. 1.
Figure 3A:
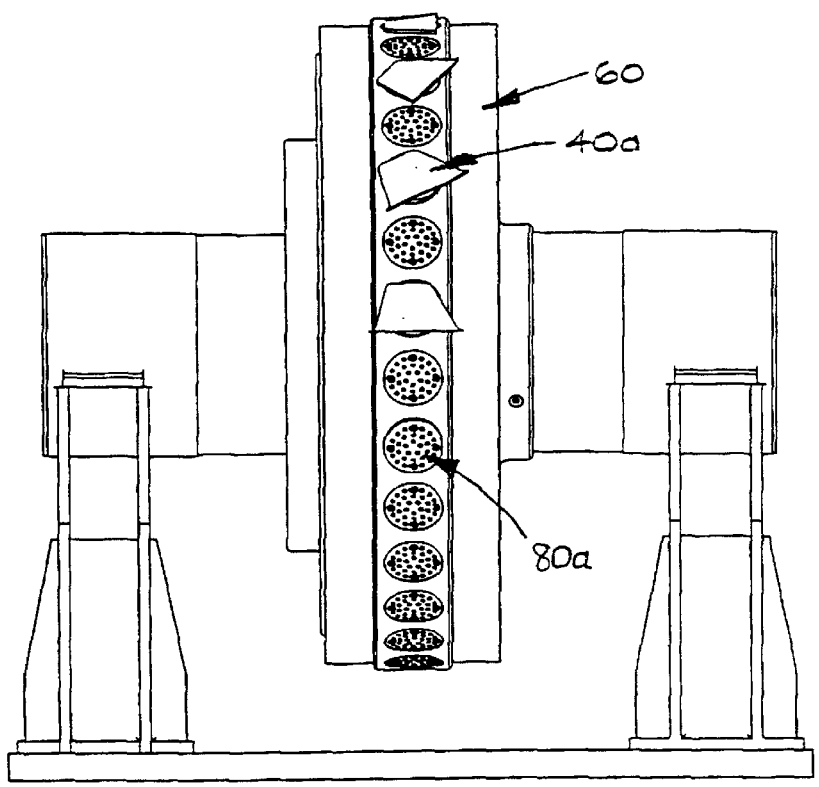
FIGS. 3a and 3b show rear and front elevation views of the apparatus of FIG. 1.
Figure 3B:
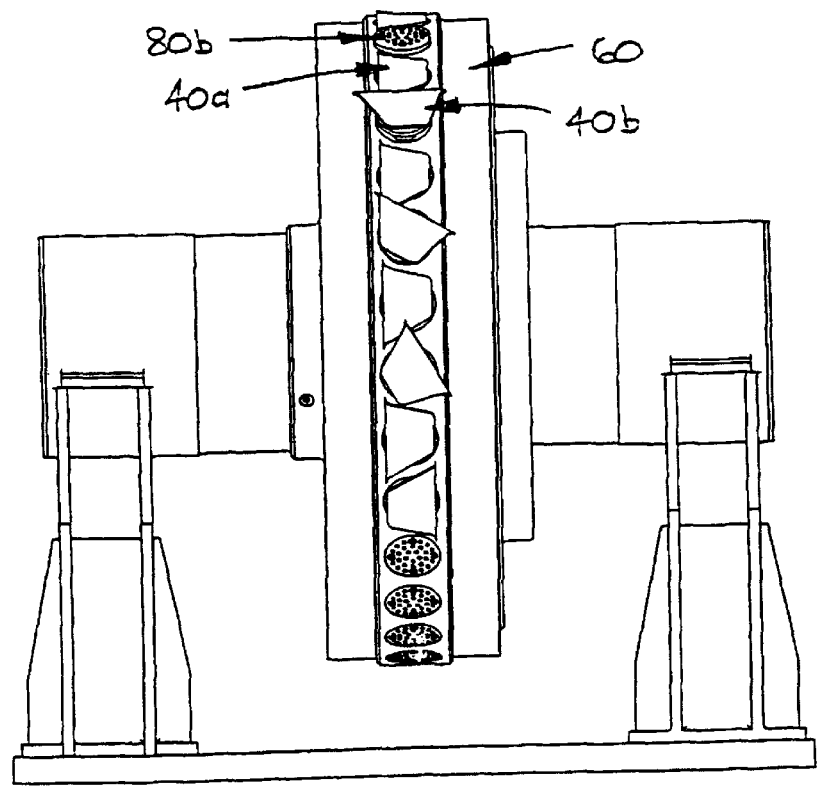

In the embodiment of the invention shown in FIGS. 1 and 2 the first and second core elements 40a and 40b are rotated through plus 90° and minus 90° respectively in order to provide an hourglass-shaped core suitable for use in an absorbent article such as a diaper.

Typically, an absorbent article is assembled from an absorbent pad element, or core which is encased between a liquid-pervious topsheet and a liquid impervious backsheet. In a preferred embodiment, the cores are comprised of airfelt or foam, within a cellulosic tissue envelope, to provide integrity to the core in use. The backsheet is coated on its inner surface with beads or spirals of adhesive, for affixing the backsheet to the core. Continuous bands of elastic are fed from metering rolls past a glue nozzle. An S-wrap arrangement of the rolls feeding the bands of elastic minimises deformation of the elastic band and allows for accurate control of the speed of the elastic. The elastic bands are fed into the direction of transport at a lower speed than the cores, the backsheet and the topsheet, so that the elastic bands are stretched.

Figure 4:
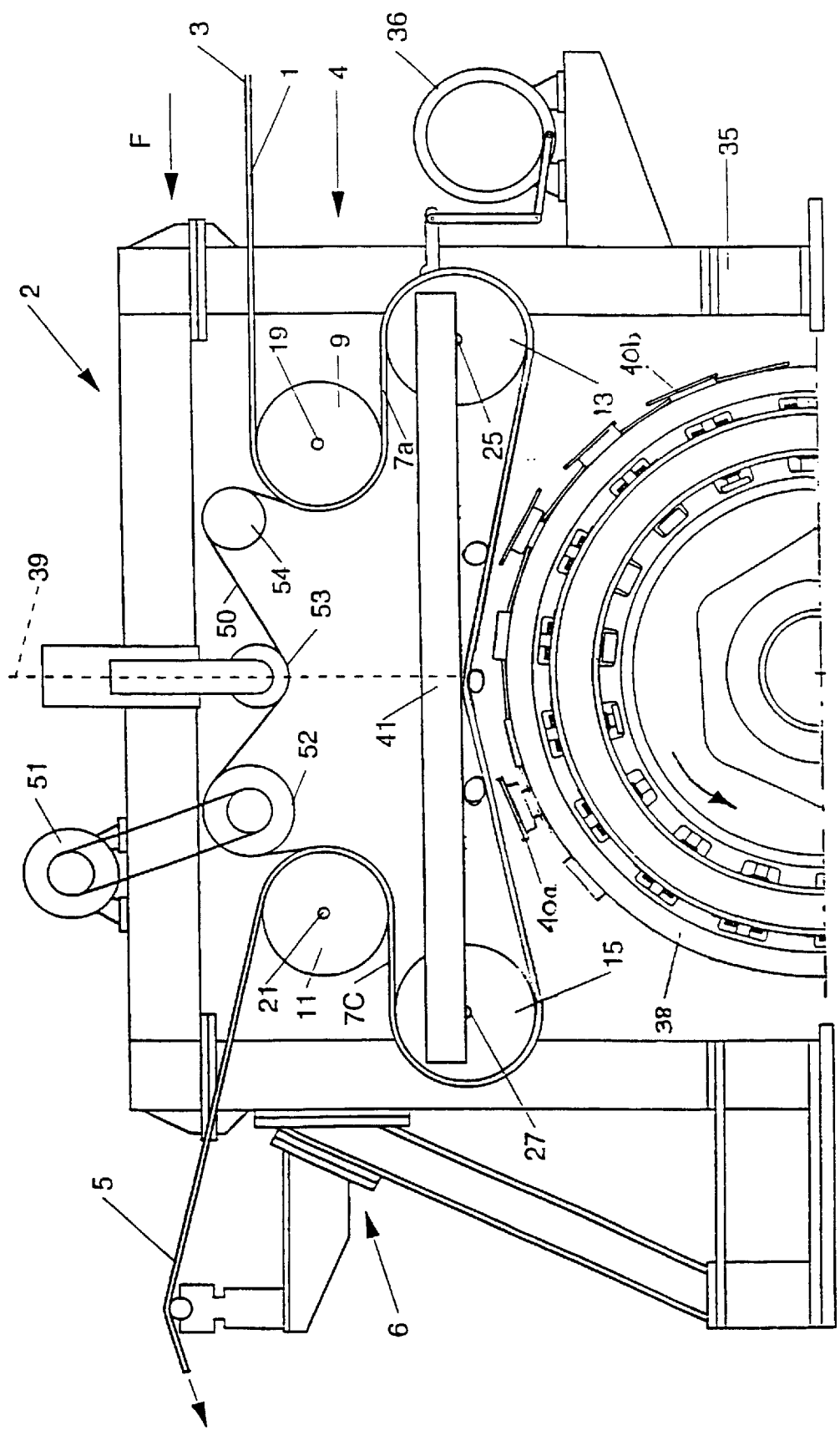
FIG. 4 shows a schematic side elevation view of a production line assembly comprising an apparatus of the present invention.

In a particularly preferred embodiment of the present invention a receiving web (which may be, for example, either the backsheet or the topsheet) passes at a constant speed of transport to the infeed side 4 of an assembly 2 for periodically changing the speed of web (illustrated in FIG. 4). In the assembly 2, the receiving web 1 can be slowed down, or stopped and is contacted by the apparatus of the invention 38. The apparatus 38 comprises means for providing the core elements. The web 1 leaves the outfeed side 6 of the assembly 2 at the constant web speed. The speed of the receiving web portions located upstream and downstream from the assembly 2 along upstream trajectory 3 and downstream trajectory 5 is not affected by the change in speed of those parts of the receiving web 1 that are passing through the assembly 2.

FIG. 4 shows the assembly 2 for changing the speed of a flexible receiving web 1 of relatively low tear strength. By flexible, it is meant that the receiving web 1 can be transported along a curvilinear trajectory and will adapt its shape so as to conform to the trajectory. The receiving web 1 is formed of flexible material, such as paper, airfelt, plastic etc. and can be comprised of the topsheet 121, the backsheet 123 or any combination thereof.

The receiving web 1 is transported along the upstream trajectory 3 with a constant velocity of transport $V_0$, in the machine direction F. The upstream trajectory 3 is formed by the length of the receiving web 1 which extends to the right of the first guide roller 9 in FIG. 4, and which is moving towards the infeed side 4 of the assembly. After passing through the assembly, the receiving web 1 exits at the outfeed side 6 and is transported at constant velocity $V_0$ along the downstream trajectory 5, which extends to the left of the guide roller 11. The upstream and downstream trajectories need not correspond to the machine direction, and can be formed by straight-line or curvilinear paths.

The guide rollers 9 and 11 are rotationally connected to the frame 35. The guide rollers 9, 11 have a fixed position. The receiving web 1 is looped around an upstream and a downstream transport roller 13, 15 which are mounted on a sled 41. The sled 41 is cyclically translated along the frame 35, generally parallel to the machine direction F, by drive motor 36.

An intermediate trajectory 7a, 7b, 7c of the receiving web 1 is located between the upstream guide roller 9 and the downstream guide roller 11, and comprises a first section 7a and a third section 7c, of variable length, located between the upstream guide roller 9 and the upstream transport roller 13 and the downstream transport roller 15 and the downstream guide roller 11 respectively. The second section 7c of the intermediate trajectory 7 is located between the transport rollers 13 and 15 and is of constant length.

Because of the symmetry of the intermediate trajectory 7a, 7b, 7c, the increase in length of the first section 7a, upon displacement of the sled 41 opposite to the machine direction F and away from the equilibrium position 39, is compensated by an equal decrease in length of the third section 7c, and vice versa. As the length of the second section 7b is constant, the whole intermediate trajectory 7a, 7b, 7c is independent of the position of the sled 41 with respect to the frame 35.

When the part of the receiving web that is located along the second section 7b of the intermediate trajectory 7a, 7b, 7c, is stationary (or at least it is slower than the speed of the web speed $V_0$) relative to the frame 35, the web 1 is contacted by the applicator means 38 which is positionally stationary (or at least slower) with respect to the frame 35. After the apparatus 38 has interacted with the receiving web 1, the web is accelerated along the section 7b of the intermediate trajectory towards the outfeed side 6 of the assembly 2, and is supplied to the downstream trajectory 5 with web speed $V_0$.

The guide rollers 9, 11 and the transport rollers 13, 15 are driven by a drive member in the form of a closed loop 50 and pulleys 52, 53 and 54. The loop 50 is partly parallel to the intermediate trajectory 7a, 7b, 7c. The loop 50 is driven at a constant speed which is equal to the speed of transport $V_0$, of the web 1 by a single drive motor 51. By driving the guide rollers 9, 11 and the transport rollers 13, 15, the strain exerted on the web 1 is minimised and can be limited to the acceleration forces, which are acting to change the speed of the web. Further details of suitable assembly are disclosed in EP-A-0 652 175, published on $10^{th}$ May 1995.

Figure 5A:
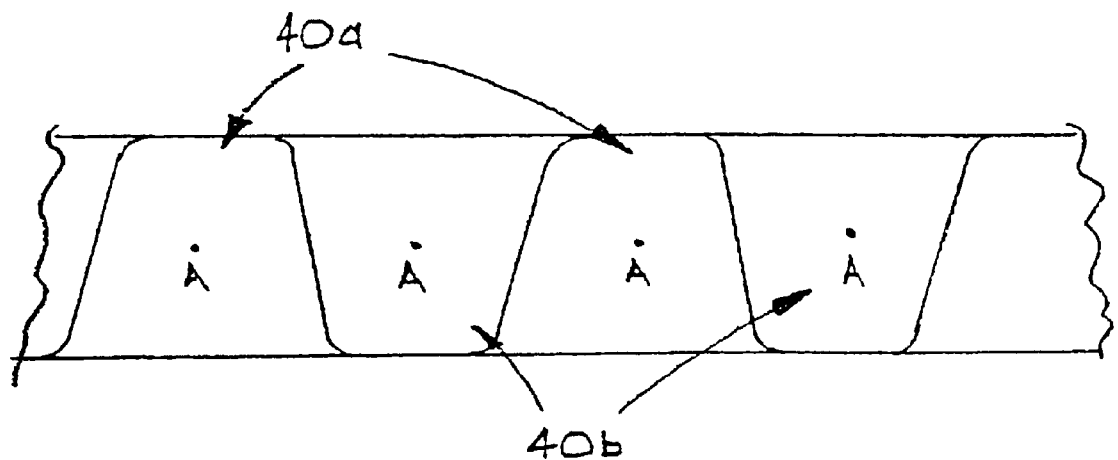
FIG. 5a shows a plan view of core elements after cutting, according to one embodiment of the process of the present invention.
Figure 5B:
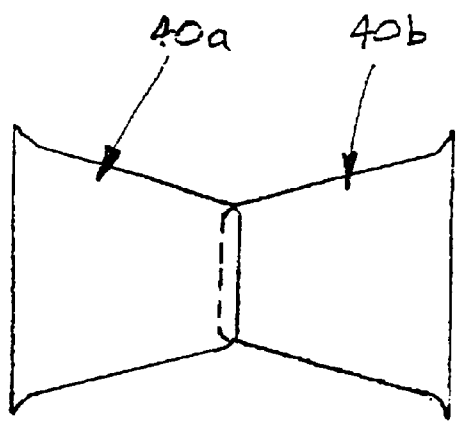

FIG. 5 shows a web 40 which has been cut into discrete core elements 40a, 40b. Second core elements 40b are subsequently rotated about their axis A.

The first and second core elements 40a, 40b are either mutually adhered, or are adhered to the receiving web 1, or both. This may be done using any conventional method such as by gluing with adhesives, such as melt adhesives, or use of self-adhesive components, or by use of ultrasonic welding, heat sealing or the like.

What is claimed is:

1. A process wherein each of the first and second core elements (40a, 40b) are rotated through 90° in mutually counter-rotating directions.

2. A process according to claim 1 wherein the continuous web (40) is made from air-laid fibers or foam.

3. A process for the manufacture of disposable absorbent cores from a continuous web (40), wherein a plurality of first and second core elements (40a, 40b), are cut from the same continuous web (40), characterised in that the absorbent core is formed by rotating each of the first and second core elements (40a, 40b) about axes (A) perpendicular to the plane of the core element (40a, 40b) and subsequently combining a first core element (40a) and a second core element (40b) in proximal relationship to form the absorbent core wherein a receiving web (1) is fed relative to a stationary frame (35) along an upstream trajectory (3), a downstream trajectory (5), and an intermediate trajectory (7a, 7b, 7c) comprised between the upstream trajectory (3) and the downstream trajectory (5), the web (1) having along the upstream trajectory (3) and along the downstream trajectory (5) a substantially constant speed of transport, wherein the receiving web (1) runs along an upstream and a downstream guide roller (9, 11) that are translationally stationary relative to the frame (35) and along an upstream and downstream transport roller (13, 15) that are periodically displaced relative to the guide rollers (9, 11) around a transfer position (39), and wherein the discrete core elements (40a, 40b) are applied to the receiving web (1) when it is at the transfer position.

4. A process according to claim 3 wherein the periodic displacement of the transport rollers (13, 15) around the transfer position occurs at a frequency of between 1 Hz and 100 Hz.

5. A process according to claim 3 wherein the receiving web (1) comprises either a liquid-pervious topsheet or a liquid impervious backsheet.

6. An apparatus (38) for the manufacture of disposable absorbent cores from a continuous web (40), wherein the apparatus comprises a means for cutting a plurality of first and second core elements (40a, 40b) from the same continuous web (40), characterised in that the apparatus further comprises means of forming the absorbent core by rotating each of first and second core elements (40a, 40b) about axes (A) perpendicular to the plane of the core element (40a, 40b) and subsequently combining a first core element (40a) and a second core element (40b) in proximal relationship to form the absorbent core and further comprising a rotating drum (60) to apply discrete first and second core elements (40a, 40b) to a receiving web (1), and further comprising vacuum shells (80a, 80b) which are arranged around the circumference of the rotating drum (60).

7. An apparatus (38) according to claim 6 wherein each of the vacuum shells (80b) are rotatable about an axis (A) perpendicular to the plane of the core elements (40a, 40b), preferably by means of rack and pinion (82, 83).

8. A process for the manufacture of disposable absorbent cores from a continuous web (40), wherein a plurality of first and second core elements (40a, 40b), are cut from the same continuous web (40), characterised in that the absorbent core is formed by rotating each of the first and second core elements (40a, 40b) about axes (A) perpendicular to the plane of the core element (40a, 40b) and subsequently combining a first core element (40a) and a second core element (40b) in proximal relationship to form the absorbent core wherein the first and second core elements (40a, 40b) are positioned in an overlapping relationship with each other.

\* \* \* \* \*

UNITED STATES PATENT AND TRADEMARK OFFICE
CERTIFICATE OF CORRECTION

PATENT NO. : 6,736,923 B1  
DATED : May 18, 2004  
INVENTOR(S) : Franzmann et al.

It is certified that error appears in the above-identified patent and that said Letters Patent is hereby corrected as shown below:

Column 5,  
Line 45, please renumber Claim "1" to read -- 2 --.  
Line 45, after "process", insert -- according to claim 1 --.  
Line 48, please renumber Claim "2" to read -- 3 --.  
Line 50, please renumber Claim "3" to read -- 1 --.

Column 6,  
Lines 18 and 22, delete "3" and insert -- 1 --.

Signed and Sealed this

Twenty-fifth Day of October, 2005

JON W. DUDAS  
*Director of the United States Patent and Trademark Office*